US00PP10743P

United States Patent [19]

Nagase

[11] Patent Number: Plant 10,743

[45] Date of Patent: Jan. 5, 1999

[54] VERBENA PLANT NAMED 'SUNMARIHO'

[75] Inventor: Yuki Nagase, Seki, Japan

[73] Assignee: Suntory Limited, Osaka, Japan

[21] Appl. No.: 756,029

[22] Filed: Nov. 26, 1996

[51] Int. Cl.[6] ..... A01H 5/00

[52] U.S. Cl. ..... Plt./87

[58] Field of Search ..... Plt./87

[56] References Cited

U.S. PATENT DOCUMENTS

| | | | |
|---|---|---|---|
| P.P. 2,404 | 5/1964 | Fujii | Plt./87 |
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,411 | 12/1995 | Tachibana et al. | Plt./87 |

*Primary Examiner*—Howard J. Locker

*Attorney, Agent, or Firm*—Burns, Doane, Swecker & Mathis, L.L.P.

[57] ABSTRACT

A new and distinct verbena variety is provided which forms attractive large yellowish-white blossoms. The plant is broad and exhibits a spreading growth habit. The blossoms are borne in abundance on spikes. The blossoming is of long duration and commonly occurs between April and November. The plant exhibits a high tolerance to rain, cold, and heat. Good resistance to diseases, such as powdery mildew, also is exhibited.

2 Drawing Sheets

BACKGROUND OF THE VARIETY

The present invention relates to a new and distinct variety of verbena plant obtained from crossing of the verbena plant (♀) which was obtained from crossing "Cristal" (♀) and a wild type of verbena plant Verbena peruviana native to Brazil (♂), and the same wild type of verbena plant *Verbena peruviana* (♂) native to Brazil.

The verbena is a very popular plant and is used for flower bedding and potting in the summer season. There are only a few varieties of the verbena plant which have a spreading growth habit, much branching, the formation of a high number of flowers in a spike and which have a high resistance to rain, heat, cold, and diseases. Accordingly, this invention was aimed at obtaining a new variety having a spreading growth habit, strong branching, the formation of a high number of flowers in a spike, a large diameter flower, high tolerance to heat and cold, and resistance to diseases and pests, and also having yellowish white flower petals.

The new variety of verbena plant according to this invention originated from crossing of the verbena plant (♀) which was obtained from crossing *Verbena hybrida "Cristal" (♀) and a wild type of verbena plant Verbena peruviana native to Brazil (♂), and the same wild type of verbena plant Verbena peruviana* (♂) native to Brazil. The new variety of the present invention is botanically classified *Verbena hybrida.*

First of all, 4 seedlings were obtained in the autumn of 1992, from crossing "CRISTAL" as female parent and a wild type of verbena plant (*Verbena peruviana*) as pollen parent in the May of 1992. These 4 seedlings were grown and the 3 seedlings were selected in view of spreading growth habit and flower petal coloration. Then 12 seedlings were obtained from crossing these 3 seedlings as female parent and the same wild type of verbena plant (*Verbena peruviana*) as pollen parent. These 12 seedlings were grown and the 4 seedlings were selected in view of spreading growth habit and flower petal coloration. And these selected 4 seedlings ware propagated by the use of cuttings, and then grown as a trial for flower bedding and planter growth beginning in the spring of 1993. Finally only one plant was selected from these 4 seedlings during such evaluation that was carried out until the autumn of 1994 and the botanical characteristics of 4 seedlings were examined, using the similar variety "Cristal" for comparison. As a result, it was concluded that this verbena is distinguishable from any other variety whose existence is known to us, is sufficiently uniform and is stable in its characteristics. This new variety of verbena plant was named "Sunmariho".

In the following description, the color-coding is in accordance with the Horticultural Colour Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The "Cristal" plant used as female parent in the crossing which resulted in the formation of this new variety "Sunmariho" variety is commercially available. The main botanical characteristics of "Cristal" are as follows.

Plant:
- *Growth habit.*—Erect.
- *Plant height.*—20–30 cm.
- *Plant extension.*—15–20 cm.

Stem:
- *Diameter.*—2.0–3.0 mm.
- *Anthocyanin pigmentation.*—Present.
- *Branching.*—Few.
- *Pubescence.*—Medium.
- *Length of internode.*—2.5–4.0 cm.

Leaf:
- *Phyllotaxis.*—Opposite.
- *Shape of blade.*—Hastate.
- *Length.*—4.0–5.5 cm.
- *Width.*—3.0–4.0 cm.
- *Depth of incision.*—Shallow.
- *Color.*—Dark yellow green (R.H.S. 146A, JHS 3508)
- *Pubescence.*—Few.

Flower:
- *Facing direction.*—Upward.
- *Outward curvature of petal.*—Slightly curved.
- *Diameter.*—1.0–2.0 cm.

*Height.*—20–30 mm.
*Color.*—Yellowish white (R.H.S. 158D, JHS 2901).
*Color intensity.*—Absent..
*Overlapping of petals.*—Opened.
*Spike.*—30–40 mm in length; and 40–55 mm in diameter.
*Calyx.*—1.5–2.0 cm in length.
*Anthocyanin pigmentation of calyx limb.*—Absent.
*Peduncle.*—1–2 mm in thickness; and 4–5 cm in length.
*Number of flowers.*—Few. (commonly 8–13).
*Reproductive organs.*—1 pistil and 4 stamens.
*Flower fragrance.*—Absent.
*Flowering duration.*—Medium.

Physiological and ecological characteristics: Low resistance to diseases and pests, low tolerances to heat, cold and rain.

The pollen parent used in the crossing which was obtained to this new variety "Sunmariho" was a wild type of verbena native to South Brazil and Verbena peruviana. This wild type of verbena plant is presently maintained at the Plant Biotechnology Laboratory of Suntory Ltd., residing at 863-1, Aza-Iketani, Oomori-cho, Youkaiti-shi, Shiga-ken, Japan.. The main botanical characteristics of this pollen parent are as follows.

Plant:
*Growth habit.*—Spreading.
*Plant height.*—10–20 cm.
*Plant extension.*—90–140 cm.

Stem:
*Diameter.*—1.0–2.0 mm.
*Anthocyanin pigmentation.*—Present.
*Branching.*—Abundant.
*Pubescence.*—Medium.
*Length of internode.*—2.5–4.0 cm.

Leaf:
*Phyllotaxis.*—Opposite.
*Shape of blade.*—Hastate.
*Length.*—2.5–3.5 cm.
*Width.*—1.5–2.0 cm.
*Depth of incision.*—Shallow.
*Color.*—Dark green (R.H.S. 137B, JHS 3716).
*Pubescence.*—Much.

Flower:
*Facing direction.*—Upward.
*Outward curvature of petal.*—Slightly curved.
*Diameter.*—1.5–3.0 cm.
*Height.*—20–30 mm.
*Color.*—Yellowish white (R.H.S. 159D , JHS 1901).
*Color intensity.*—Absent.
*Overlapping of petals.*—Opened.
*Spike.*—30–40 mm in length; and 55–65 mm in diameter.
*Calyx.*—1.5–2.0 cm in length.
*Anthocyanin pigmentation of calyx limb.*—Absent.
*Peduncle.*—1–2 mm in thickness; and 3.0–4.5 cm in length.
*Number of flowers.*—Plentiful (commonly 10–14).
*Reproductive organs.*—1 pistil and 4 stamens.
*Flower fragrance.*—Absent.
*Flowering duration.*—Medium.

Physiological and ecological characteristics: High resistance to diseases and pests, high tolerances to heat, cold and rain.

This new variety of verbena plant "Sunmariho" was asexually reproduced by cuttings at the Plant Biotechnology Laboratory of Suntory Ltd., 863-1, Aza-Iketani, Oomori-cho, Youkaiti-shi, Shiga-ken, Japan, and the homogeneity and stability thereof were confirmed.

SUMMARY OF THE VARIETY

This new variety of verbena plant has a spreading growth habit having long stems. A broad plant is formed. The plant has abundant branching and an abundant number of flowers in a spike, with a great profusion of blooms. The Blooming period is from late April to November and the flowering duration is long. The entire bush remains in bloom for a considerable period of time. The flower size is large and the petal coloration of the flowers is yellowish white color. The plant is highly tolerant to cold and heat, exhibits a high resistance to pests and diseases, is particularly resistant to powdery mildew and rain.

DESCRIPTION OF THE VARIETY

Figure 1:
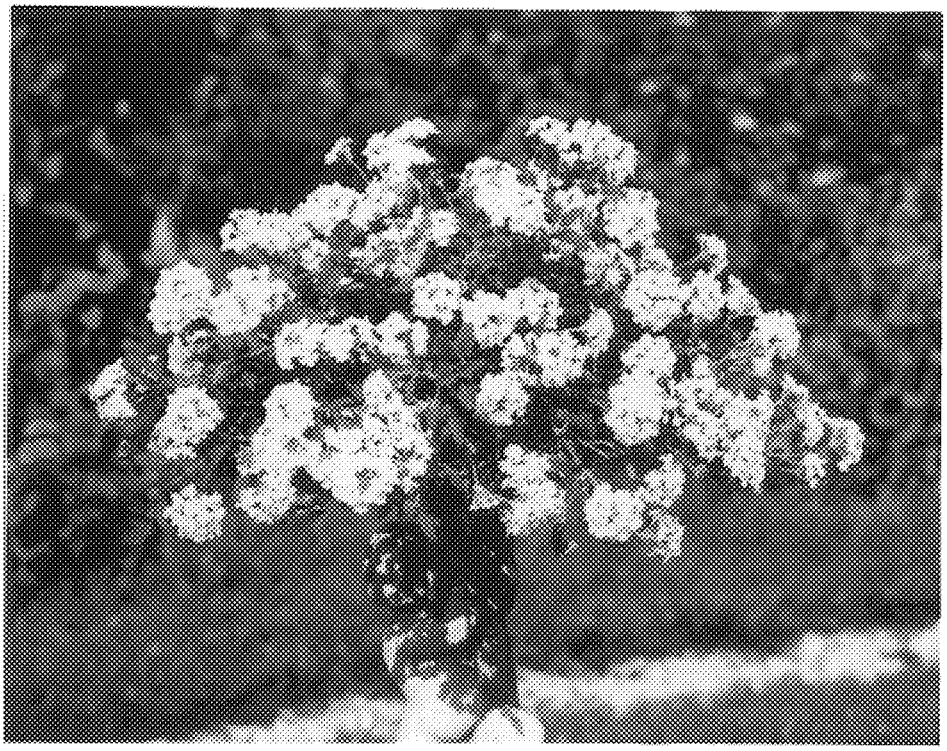
FIG. 1 is photograph giving a partial view of the new variety of verbena plant while planted in a flower pot.
Figure 2:
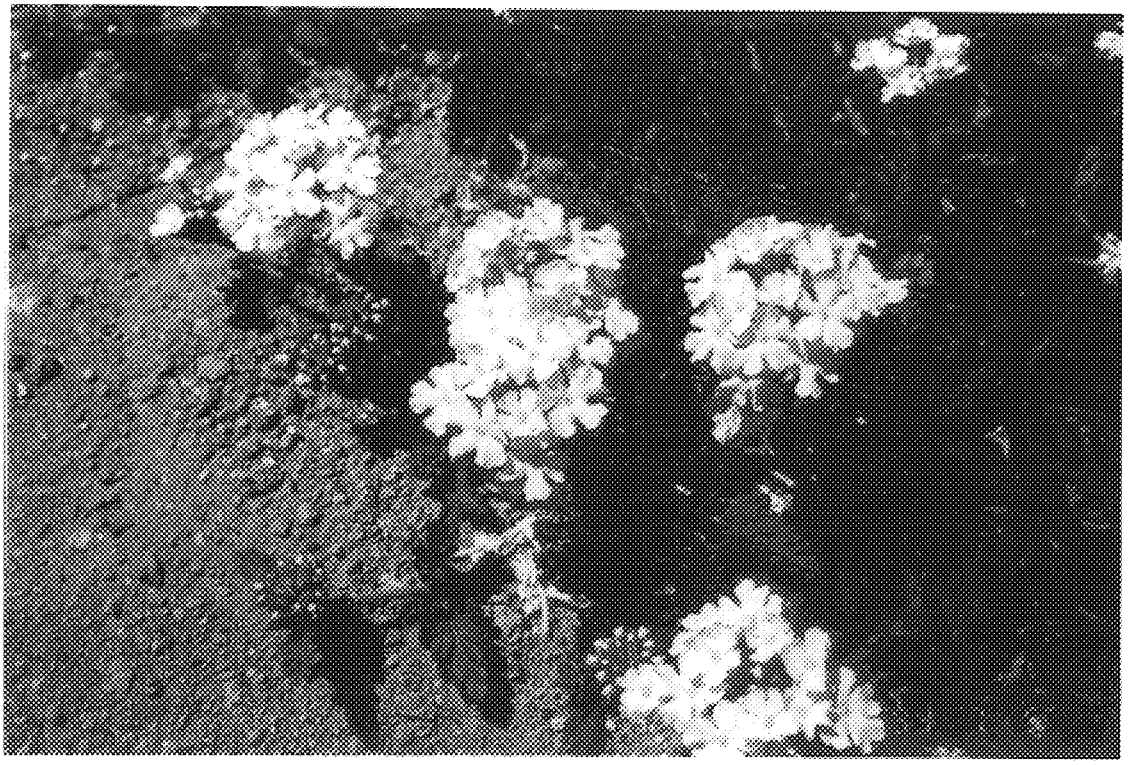
FIG. 2 is a photograph of the flowers of the new variety of verbena plant.

The botanical characteristics of the new and distinct variety of verbena plant, "Sunmariho" are as follows.

Plant:
*Growth habit.*—Spreading.
*Plant height.*—10–20 cm.
*Plant extension.*—50–80 cm.
*Growth.*—Very vigorous with abundant branching and a great profusion of blooms; and with the whole bush remaining in bloom for considerable period of time.

Stem:
*Diameter.*—2.0–3.0 mm.
*Anthocyanin pigmentation.*—Present.
*Branching.*—Abundant.
*Pubescence.*—Medium.
*Length of internode.*—2.0–4.0 cm.

Leaf:
*Phyllotaxis.*—Opposite.
*Shape of blade.*—Hastate.
*Length.*—4.0–6.0 cm.
*Width.*—2.0–3.0 cm.
*Depth of incision.*—Shallow.
*Color.*—Dark yellow green (R.H.S. 146A, JHS 3508)
*Pubescence.*—Medium.

Flower:
*Facing direction.*—Upward.
*Outward curvature of petal.*—None.
*Diameter.*—5–2.0 cm.
*Height.*—20–30 mm.
*Color.*—Yellowish white (R.H.S. 159D, JHS 1901). Such coloration is substantially the same on both surfaces of the petals, at the throat of the corolla, and at the area where an eye would appear if present. Accordingly, the new variety possesses no eye.
*Color intensity.*—Absent.
*Overlapping of petals.*—Opened.
*Spike.*—30–50 mm in length; and 40–60 mm in diameter.
*Calyx.*—1.0–2.0 cm in length.
*Anthocyanin pigmentation of calyx limb.*—Absent.

*Peduncle.*—1–2 mm in thickness; and 4.0–5.0 cm in length.

*Number of flowers.*—Plentiful (10–15).

*Reproductive organs.*—1 pistil and 4 stamens.

*Flower fragrance.*—Absent.

*Flowering duration.*—Long.

Physiological and ecological characteristics: High resistance to diseases and pests, particularly to powdery mildew. High tolerance to heat and cold is exhibited. High tolerance to rain is exhibited. Upon self-pollination viable seed forms on the plant of the new variety of the present invention. However, such seed does not form plants identical to the new variety since the new variety is an $F_1$ hybrid.

Pinching of the blossoms is not necessary to ensure continued blooming. It is found that such pinching will increase the number of blooms that are formed.

This new variety of verbena plant is most suitable for growing as flower bedding and as a pot plant in planters and is further particularly well suited for growing as a ground cover. When the new variety of the present invention is compared to the 'Snow Carpet' variety (U.S. Plant Pat. No. 2,404), it is found that the new variety forms blossoms that consistently are yellowish white in coloration and that the blossoms of the 'Snow Carpet' variety are white with a pale yellow eye.

The plant of this new variety, "Sunmariho" is presently planted and maintained at the Plant Biotechnology Laboratory of Suntory Ltd., 863-1, Aza-Iketani, Oomori-cho, Youkaiti-shi, Shiga-ken, Japan.

I claim:

1. A new and distinct variety of verbena plant having the following combination of characteristics:

(a) exhibits a spreading growth habit with long stems,
(b) forms in abundance on spikes attractive large yellowish-white blossoms over an extended period of time,
(c) exhibits a high tolerance to rain, cold and heat, and
(d) exhibits good resistance to powdery mildew;

substantially as illustrated and described.

* * * * *

SUNMARIHO

SUNMARIHO